United States Patent [19]

Zonneveld

[11] Patent Number: 4,792,124
[45] Date of Patent: Dec. 20, 1988

[54] SUB-LANCE INSTALLATION FOR CARRYING OUT MEASUREMENTS AND/OR TAKING SAMPLES IN A METALLURGICAL FURNACE

[75] Inventor: Petrus C. H. Zonneveld, Heemskerk, Netherlands

[73] Assignee: Hoogovens Groep B.V., IJmuiden, Netherlands

[21] Appl. No.: 154,295

[22] Filed: Feb. 10, 1988

[30] Foreign Application Priority Data

Feb. 16, 1987 [NL] Netherlands .......................... 8700371

[51] Int. Cl.<sup>4</sup> .............................................. C21C 5/28
[52] U.S. Cl. ....................................... 266/226; 266/79
[58] Field of Search ...................... 266/226, 79, 80, 87; 73/863.11, DIG. 9

[56] References Cited

U.S. PATENT DOCUMENTS 4,097,031 6/1978 Higuchi et al. ...................... 266/226
4,141,249 2/1979 Ishikawa et al. ................ 73/DIG. 9
4,438,653 3/1984 Beentjes .......................... 73/DIG. 9

Primary Examiner—L. Dewayne Rutledge
Assistant Examiner—S. Kastler
Attorney, Agent, or Firm—Stevens, Davis, Miller & Mosher

[57] ABSTRACT

Sub-lance installation for carrying out measurements and/or taking samples in a metallurgical furnace, has an elongate tubular lance which is rotatable around its longitudinal axis and is attached at its upper end with its longitudinal axis vertical to a carriage by means of which the lance is moved vertically, the installation also including means for rotating the lance about its longitudinal axis. In order that the rotation of the sub-lance can be achieved by a robust apparatus, which does not itself require power and can operate automatically, said means for rotating the lance comprises a helical guide system which imparts rotation to the lance. The helical guide system comprises mutually cooperating helical projections and recesses mounted respectively on the lance and a guide for the lance.

9 Claims, 3 Drawing Sheets

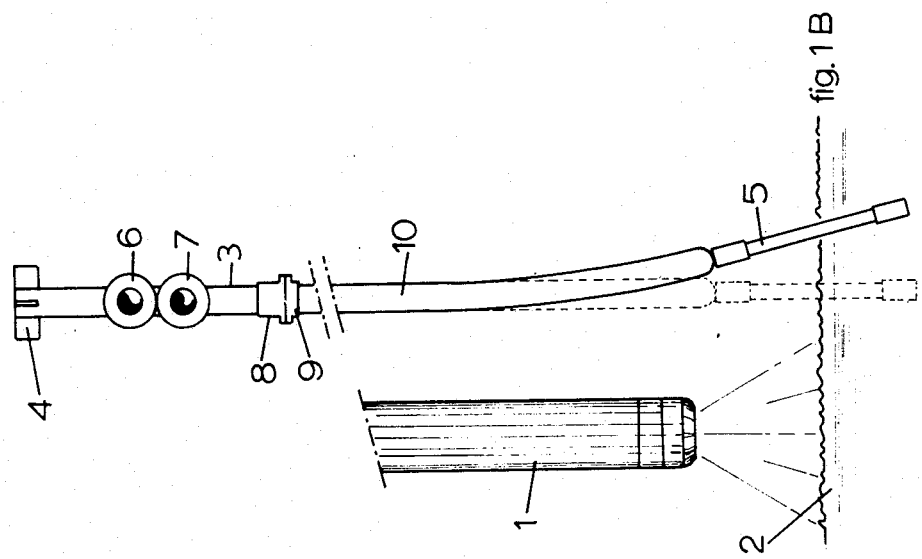
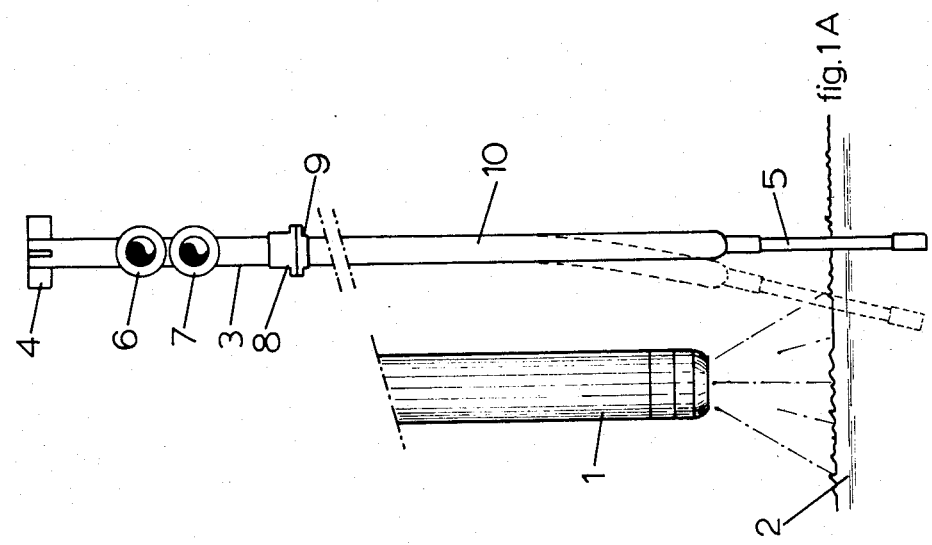

SUB-LANCE INSTALLATION FOR CARRYING OUT MEASUREMENTS AND/OR TAKING SAMPLES IN A METALLURGICAL FURNACE

BACKGROUND OF THE INVENTION

1. Field of the Invention

The invention relates to a sub-lance installation for carrying out measurements and/or taking samples in a metallurgical furnace, comprising an elongate tubular lance which is rotatable around its longitudinal axis and which is attached at its upper end to a carriage by which the lance with its longitudinal axis vertical is moved vertically to bring its lower end to an operational location for measurement and/or sample-taking.

The invention will be described in particular for application in a steel converter of the type in which liquid pig iron is made into steel by blowing in oxygen from above through a main lance onto the pig iron bath, but the invention is not limited to this application. Applications of the invention are possible in metallurgical processes in other types of metallurgical furnace.

2. Description of the Prior Art

In order to be able to monitor and control as necessary the progress of the refining process in the steel furnace during the oxygen blowing, use is often made of a sub-lance. During the oxygen blowing, or during an interval in the oxygen blowing, the sub-lance is moved downwards parallel to the main lance, until a probe carried by the sub-lance, extends into the bath. The probe can be equipped for example with means for measuring the bath temperature and/or for analysing the concentration of particular elements such as carbon or oxygen in the bath. The results of this measurement can then be passed from the probe via a cable through the sub-lance to a point outside the furnace. It is also possible to use a probe in the form of a sampling pot, in which case the sub-lance can extract a sample from the bath, which can then be analysed outside the furnace.

The use of sub-lances for carrying out measurements and/or for taking samples has been described in detail in the literature. Some examples are given below.

One difficulty arising in the use of a sub-lance is that the sub-lance, when it is near the blowing lance, is heated by the furnace asymmetrically. This causes distortion of the sub-lance with the result that it is only suitable for a few measurements. A customary method of overcoming this difficulty is to remove the sub-lance from its suspension after use and straighten it elsewhere. After this it an be suspended again and used for a subsequent operation. It is obvious that for this reason the effectiveness of the sub-lance is limited and that its operation and preparation involve much work. In particular, if the sub-lance is of the liquid cooled type, it is necessary when straightening it that the connections for liquid cooling be first removed and then fitted back in place.

A sub-lance, in which the difficulty just described is avoided, is known for example from U.S. Pat. No. 4,438,653 in which the sub-lance is rotatable about its vertical longitudinal axis. This makes it possible, after the sub-lance has been used and consequently been distorted, to rotate the sub-lance. In the next operation using the sub-lance it will bend back again to its original straight condition and then distort again, after with the sub-lance can be rotated once again. In this particular known sub-lance the rotation is done by hand using a special spanner. The difficulty of this is that in practice the rotation is often forgotten and that the spanner can be mislaid. The rotation is in any case labour-intensive and difficult to combine with a production function.

Another arrangement for the rotation of the sub-lance is shown in U.S. Pat. No. 4,141,249, wherein means for rotating the sub-lance are used, which comprise a driving motor and gear wheels. The difficulty of this arrangement is that, when rotating the sub-lance, large eccentric forces are applied to the sub-lance so that there is a danger of the cooling water connections of the sub-lance leaking. The drive, which rises and falls with the sub-lance and which has to have power supplied from the outside forms a rather complicated and vulnerable entity liable to failure under the operating conditions, which is undesirable.

SUMMARY OF THE INVENTION

The object of the invention is to provide a sub-lance installation of the type in which the difficulties of distortion of the sub-lance are overcome by rotating the sub-lance in which the means for rotating the sub-lance are robust, in which eccentric forces applied to the sub-lance during the rotation may be small or zero, in which for the purpose of rotation no energy is supplied to the means for rotating the sub-lance and in which the rotation can take place automatically.

According to the invention, the sub-lance installation has means for rotating the lance comprising a helical guide system which imparts rotation to the lance. Preferably the helical guide system comprises at least one pair of cooperating projection and recess one of which is helical and which are mounted on the lance and on a guide for the lance, the lance being caused to rotate by relative movement with respect to the guide. Preferably the guide is fixed and the rotation of the lance takes place during the vertical movement of the lance relative to the guide. The guide is preferably mounted on a vertical guide path for the lance near its lower end.

The sub-lance rotating system according to the invention can be simple and robust. The rotation of the sub-lance can take place during the normal use of the sub-lance and does not therefore take up production time. The energy needed for rotating the sub-lance is can be supplied by the vertical movement of the sub-lance and thus does not need to be supplied separately.

In on preferred embodiment, the helical guide system comprises at least two helical projections arranged spaced peripherally on the outer surface of the lance, extending helically over a peripheral angle of 180 degrees. Consequently no eccentric forces are applied to the sub-lance during rotation. The helical projections are located fitted between the bottom and top ends of the lance and may have, at their bottom and top ends, continuations extending parallel to the longitudinal axis of the lance, over a considerable length. These continuations form a run-in and run-out for the helical guide elements, which guarantees that even if the sub-lance has to be lowered ever deeper into the converter during a campaign of the furnace, as the refractory lining of the converter wears, rotation of the sub-lance can still take place. The projections may consists of strips welded to the outer surface, e.g. the outer sheath, of the lance. If for example round bar material bent into helical shape is used for the strips, a very cheap construction is obtained.

Preferably the said guide system of the helical guide system at least partly surrounds the outer surface of the lance in the peripheral direction, and the recesses of the helica guide system cooperating with the projections comprise grooves in the internal surface of the guide facing the lance. In this embodiment extremely simple construction is obtained.

Preferably, the guide of the guide system can be opened and closed in order to determine whether or not the lance is rotated. The guide system may be equipped with a pneumatic cylinder for opening and closing. The pneumatic cylinder can be controlled by a PLC (programmable logic control). By this means the sub-lance can be rotated as required, and control of the rotation can be automated. When the lance is lowered it is rotated in one direction. When the lance is raised it is rotated in the opposite direction. By opening the guide system when the lance is being lowered or when it is being raised, it is possible to cause the lance to be rotated always in the same direction. However, by rotating the lance alternately when lowering and raising it is possible to prevent the measuring cable of the lance leading to the exterior being damaged by twisting.

BRIEF INTRODUCTION OF THE DRAWINGS

A preferred embodiment of the invention will now be described by way of non-limitative example, with reference to the accompanying drawings, in which:

FIGS. 1a and 1b are schematic views of a sub-lance at various phases in its use.

DESCRIPTION OF THE PREFERRED EMBODIMENT

Figure 2:
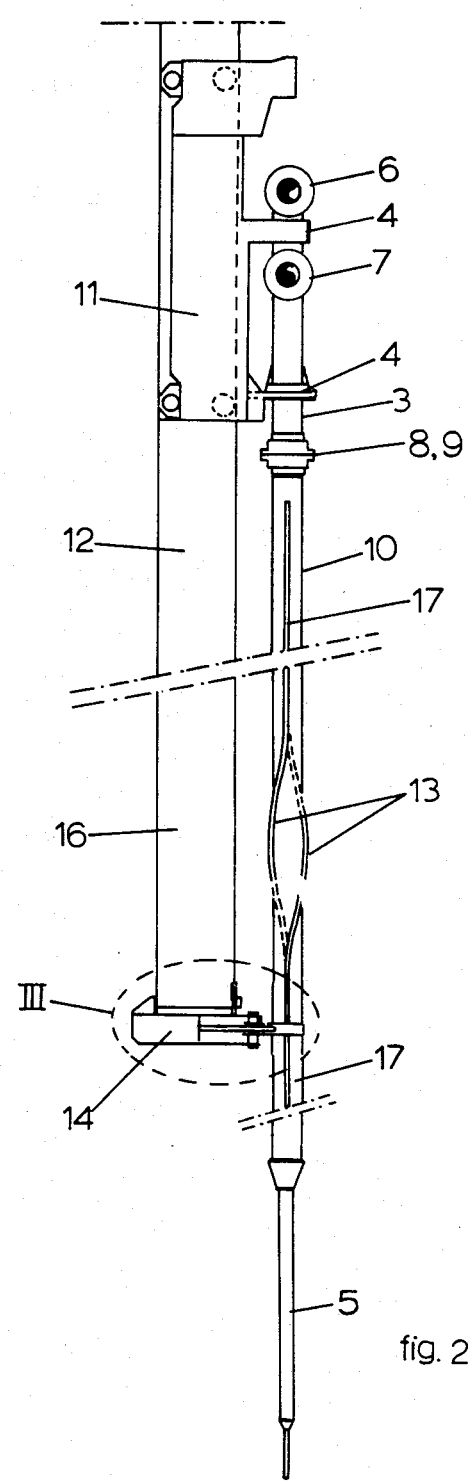
FIG. 2 shows the preferred embodiment of means for rotating a sub-lance in a sub-lance installation according to the invention.

FIGS. 1a and 1b show a main lance 1 which blows oxygen onto a metal bath 2. Parallel with the oxygen lance 1 is a sub-lance 3 shown in its lowest position, in which a probe 5 at its lower end extends into the bath. The sub-lance 3 is an elongate tubular structure and has its longitudinal axis vertical. At the top end of the sub-lance 3 suspension means 4 are fitted which suspend the sub-lance in a carriage by which the sub-lance can be moved upwards and downwards along a guide path. An inlet 6 and outlet 7 for cooling liquid are arranged near the top end, through which the sub-lance can be cooled almost as far as the attachment for the probe 5 by means of liquid flowing through it.

The sub-lance 3 is of the rotable type and in FIGS. 1 and 2 is shown in an embodiment such as is known from U.S. Pat. No. 4,438,653. The outer sheath 10 of the sub-lance is divided, the two parts being joined to each other by the coupling halves 8 and 9. The coupling halves 8 and 9 are rotatable with respect to each other and provided with a seal in order to prevent leakage of the cooling liquid. The invention can however not only be applied to this embodiment of a sub-lance, but also to other embodiments, for example to the rotatable sub-lance such as is known from U.S. Pat. No. 4,141,249.

In FIG. 1a the position of the sub-lance for blowing of oxygen onto the bath is shown by solid lines. The sub-lance is then still straight. During the blowing of oxygen the sub-lance is heated on one side in such a way that after the oxygen blowing, it is distorted and assumes the position shown by the broken lines. If the sub-lance is now rotated through 180 degrees about its vertical axis for the next charge of the furnace, the sub-lance as when lowered the position shown in FIG. 1b by solid lines. After further blowing has taken place onto the bath the sub-lance is bent back by the heat so that it is once more straight, as shown in FIG. 1b by broken lines. Between the end of this blowing and the next charge no rotation of the sub-lance is necessary, because the lance is now in the position and shape as in the initial position of FIG. 1a. After the next operation in which the sub-lance is used, however, it will be bent again and it must be rotated once more. If this practice is established, it is therefore sufficient for the sub-lance to be rotated through 180 degrees each time after being used twice.

It has become clear in practice that this distortion takes place mainly during so called in-blow measurement, in which measurement takes place during the oxygen blowing, in other words without a pause in the blowing. Precisely this in-blow measurement is of essential importance in order to guarantee fully dynamic operation of the furnace and in order to obtain a yield as high as possible in the recovery of oxygas. It has also become clear that the distortion of the sub-lance occurs somewhat more gradually than is set out above schematically. It has however appeared necessary to rotate the sub-lance at least once per working shift because otherwise serious problems occur with insertion of the probe.

FIG. 2 shows a preferred embodiment of the invention. Corresponding reference numbers in FIGS. 1, 2 and 3 refer to corresponding elements.

In FIG. 2 the sub-lance 3 is shown suspended from the carriage 11 by means of which the sub-lance can be lowered and raised into the converter (not shown) along a vertical guide system 12. The sub-lance is equipped with a helical guide path in order to rotate it, which in the preferred embodiment shown in FIG. 2 comprises guide elements in the form of two helical projections 13 each extending helically over a circumferential length of 180 degrees and mounted diametrically opposite each other on the outer sheath 10 of the sub-lance. The helical guide system also has a guide 14 for the sub-lance, which partly surrounds the sub-lance and has recesses 15 (FIG. 3), which cooperate with the helical projections 13. The guide 14 is fixed to the vertical guide path 12 near its lower end 16. By the interaction of the projections 13 and recesses 15, for example, on lowering of the sub-lance from the position shown in FIG. 2, rotation of the sub-lance through 180 degrees about its vertical axis takes place. Rotation takes place also on raising the sub-lance from the lowered position. For this rotation no separate drive is necessary, whilst no eccentric forces will be exercised on the sub-lance.

The invention extends not only to the preferred embodiment shown in FIG. 2 but also to variants in which for example projections are mounted on the guide 14 and cooperating recesses on the sub-lance, these guide elements together forming a helical guide system. It is also possible for example for the guide not to be mounted rigidly but for lance and guide system to have a relative movement with respect to each other, for example the guide can be raised whilst the sub-lance is being lowered.

As shown the helical projections 13 are arranged between the bottom and top ends of the sub-lance, and above and below the projections 13 there are continuations 17 of the projections extending parallel with the longitudinal axis of the sub-lance, which serve as run-in and run-out. These continuations are of considerable length because the sub-lance, as the furnace campaign proceeds, has to be lowered for measuring further into the converter because the lining of the converter wears away.

Figure 3:
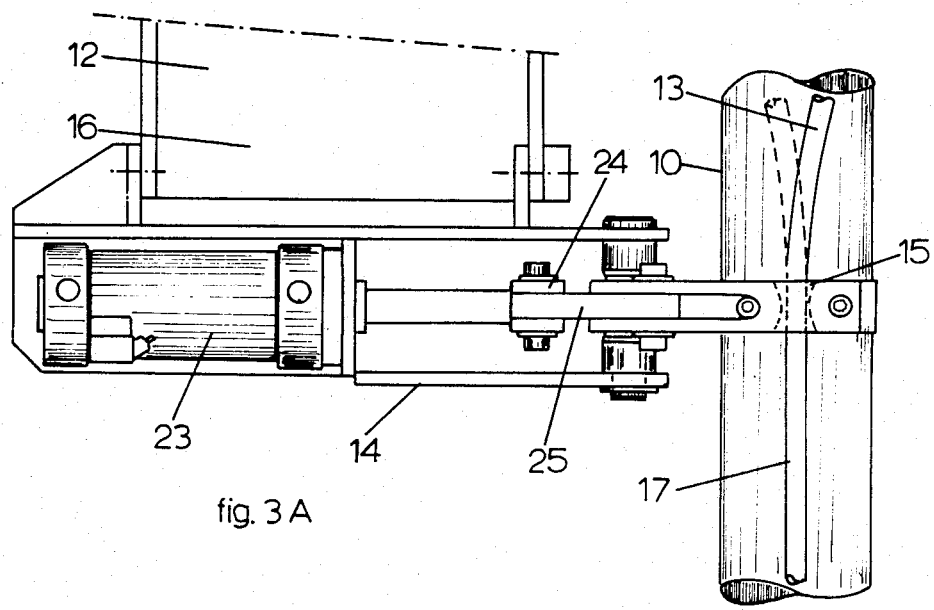
FIGS. 3a and 3b are side and top views of the guide forming part of the means for rotating the sub-lance at detail III in FIG. 2.
Figure 3:
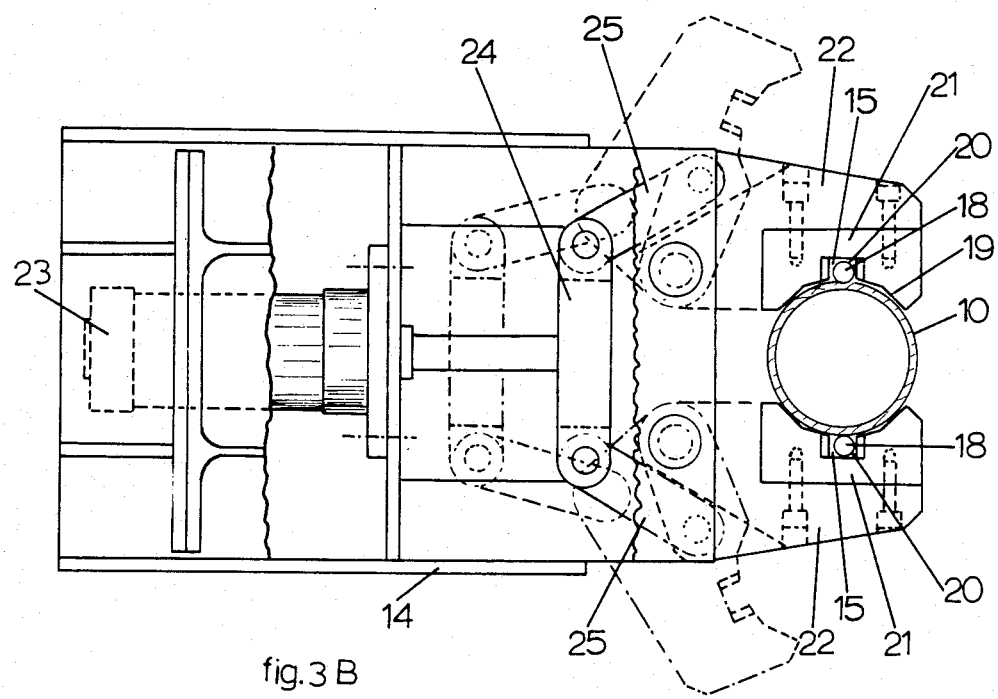

As shown in FIG. 3 the projections consist of strips or lengths 18 of round bar material welded to the outer sheath 10. The guide 14 has an internal surface 19, which envelops the outer sheath 10 of the sub-lance at least partially and in which the grooves 20 forming the recesses 15 interacting with the projections 18 are formed. In the grooves sliding friction occurs. The grooves are made in blocks 21 of material which must be resistant to this sliding. Naturally, there are also variants of the invention in which the projections 18 and possibly also the outer sheath 10 are guided by rollers.

As will further be seen from FIG. 3, the guide 14 comprises a pair of claws 22, in whose opposed surfaces the recesses 15 are provided. The claws 22 can be opened add closed by means of a pneumatic cylinder 23, via a yoke 24 and lever 25 in order to release the sub-lance. When released from the guide 14, the sub-lance 3 is not rotated when it moves vertically. Thus control of the rotation of the sub-lance is effected via the pneumatic cylinder 23.

What is claimed is:

1. Sub-lance installation for performing at least one of carrying out measurements and taking samples in a metallurgical furnace, having
    (a) an elongate tubular lance having a vertical longitudinal axis, an upper end and a lower end and being rotatable about said longitudinal axis,
    (b) a carriage to which said lance is attached at its upper end and by which said lance is movable vertically so as to bring said lower end into an operational location in the furnace for at least one of measurement and sample-taking,
    (c) means causing rotation of said lance about its longitudinal axis comprising a helical guide system which imparts said rotation to the lance, said helical guide system comprising a guide for the lance and at least one pair of guide elements in the form of mutually cooperating projection and recess at least one of which is helical and one of which is on the lance and the other of which is on said guide for the lance, said rotation of the lance being caused by cooperative action of said projection and recess upon relative movement of the lance and the guide.

2. Sub-lance installation according to claim 1 wherein said guide has a fixed vertical location and said rotation of the lance is caused when the lance is moved vertically by said carriage.

3. Sub-lance installation according to claim 2 having a vertical guide path for the vertical movement of the lance, said guide path having a lower end and said guide being mounted at the lower end of the guide path.

4. Sub-lance installation according to claim 1 wherein said guide system has at least two said projections which are helical and are mounted on the outer surface of the lance spaced circumferentially from each other around the lance and each extends helically along the lance over a circumferential angle of 180° said guide of the guide system having correspondingly at least two said recesses.

5. Sub-lance installation according to claim 4 wherein each said helical projection has, at its upper and lower ends, continuations extending parallel to the longitudinal axis of the lance.

6. Sub-lance installation according to claim 4 wherein the projections are elongate members welded to the outer surface of the lance.

7. Sub-lance installation according to claim 1 wherein said guide of the guide system surrounds at least part of the periphery of the lance and has at least two of said recesses in the form o grooves on its surface facing the lance and spaced apart around the lance.

8. Sub-lance installation according to claim 1 wherein said guide of the guide system at least partly surrounds the lance and is openable and closable to allow release or rotation of the lance.

9. Sub-lance installation according to claim 8 wherein the guide is provided with a pneumatic cylinder for opening and closing it.

* * * * *